United States Patent [19]

Suzuki et al.

[11] Patent Number: 4,906,578
[45] Date of Patent: Mar. 6, 1990

[54] AEROBIC-CULTIVATION TANK

[75] Inventors: Akira Suzuki; Hiroyoshi Konno; Shigeo Kono, all of Tokyo, Japan

[73] Assignee: Kirin Beer Kabushiki Kaisha, Tokyo, Japan

[21] Appl. No.: 290,993

[22] Filed: Dec. 28, 1988

[30] Foreign Application Priority Data

Jan. 8, 1988 [JP] Japan .................................. 63-1834

[51] Int. Cl.⁴ .............................................. C12M 1/10
[52] U.S. Cl. .................................. 135/316; 435/285; 435/287; 435/313; 165/169
[58] Field of Search ............... 435/316, 287, 313, 311, 435/315, 285; 422/231, 224; 165/168, 169

[56] References Cited

U.S. PATENT DOCUMENTS 3,460,810 8/1969 Mueller ............................ 435/316 X
3,681,200 8/1972 Ridgeway, Jr. .................... 435/311
4,746,615 5/1988 Buchholz et al. ................. 435/313 X

FOREIGN PATENT DOCUMENTS

2441334 3/1975 Fed. Rep. of Germany ...... 435/316
456827 2/1975 U.S.S.R. ........................... 435/316

Primary Examiner—Larry Jones
Attorney, Agent, or Firm—Ladas & Parry

[57] ABSTRACT

An aerobic-cultivation tank of vertical type comprises: a closed outer tank structure of cylindrical shape; an internal cooling jacket secured concentrically to the inner wall surface of said tank structure and having a cylindrical space for accommodating a coolant; a plurality of fluid downcast pipes passed vertically through said space and being open at upper and lower ends thereof to upper and lower interior parts of the tank structure; means for passing the coolant through said space; and means for supplying fluid media into the tank structure, whereby, when the fluid media are supplied into the tank structure to a level above the upper ends of the fluid downcast pipes, the fluid media overflow into and descend through said pipes, while being cooled, into a lower interior part of the tank, while a portion of said fluid media in contact with the inner surface of the cooling jacket is also cooled and descends, the fluid media body as a whole thereby undergoing a natural circulatory flow due to convection.

9 Claims, 7 Drawing Sheets

AEROBIC-CULTIVATION TANK

BACKGROUND OF THE INVENTION

This invention relates to aerobic-cultivation tanks and more particularly to an aerobic-cultivation tank for cultivating microorganisms such as baker yeast, fodder yeast, and single-cell proteins (S.C.P.s).

Among cultivation tanks, tanks for propagation of microbes, in comparison with tanks for fermentation for the production of alcohol, are accompanied by the problem of a great quantity of heat generated therein by reaction. For this reason, operational control for maintaining an appropriate temperature in such a tank is required in order to prevent the microbes from losing viabilities. In the case of a cultivation tank of large capacity, however, sufficient cooling cannot be achieved by merely installing a water-cooled jacket because of insufficient area for heat transmission. For overcoming this difficulty, various cooling methods and systems have heretofore been proposed and reduced to practice.

Representative examples of known cooling means of cultivation tanks are those of the Waldhof type, the Frings type, and the Vögelbusch type. In each of the cooling systems of these types, a cooling pipe in the shape of a coil is installed within the cultivation tank, and a coolant is passed through this cooling pipe thereby to cool the fluid media in the tank. In another known type of cooling means, a part of a circulatory system containing a cooling liquid is passed through the cultivation tank and a cooler is installed in the system in a part thereof outside the tank.

The known tanks of these types, however, tend to have complicated construction as a whole. In a tank having therein a coil-shaped cooling pipe, not only is the construction complicated, but the washability (self-flushing characteristic) of its interior is very poor and gives rise to problems.

SUMMARY OF THE INVENTION

Accordingly, it is an object of this invention to provide an aerobic-cultivation tank which, while possessing excellent washability, sanitation, and liquid circulation, has a large heat-transmission area and high cooling efficiency.

According to this invention, briefly summarized, there is provided an aerobic-cultivation tank of vertical type comprising: a closed outer tank structure of cylindrical shape having upper, middle, and lower parts; a cooling jacket disposed within said middle part of said tank structure and comprising a part of the tank structure, a hollow cylindrical inner wall disposed concentrically within the tank structure with a cylindrical space therebetween, and upper and lower annular plates respectively fixed to upper and lower parts of said inner wall and to the tank structure and closing the upper and lower ends of said space, which is thereby sealed apart from the remainder of the interior of the tank structure; a plurality of fluid downcast pipes disposed vertically with regular distribution in and around said space and, at the upper and lower ends thereof, passed through and fixed to said plates, said pipes having open ends communicating with the interiors of the upper and lower parts of the tank structure; means for passing a coolant through said space of the cooling jacket; and means for supplying fluid media into the interior of the tank structure, whereby when fluid media are supplied into the tank structure interior to a level above said upper annular plate, said fluid media overflow into and descend through said fluid downcast pipes, while being cooled, into said lower part, while a portion of the fluid media in contact with the inner wall surface of said inner wall is also cooled and descends, the fluid media as a whole thereby undergoing a natural circulatory flow.

The fluid media are caused by aeration, agitation, or other action to rise in the central part of the tank structure and to flow radially outward at the upper part of the body of the fluid media. Then, as it contacts the inner wall surface of the cooling jacket installed around the inner side of the tank structure, the fluid media are cooled and flow downward. Thus a natural convectional flow is established. Furthermore, a portion of the fluid media at the surface thereof overflows into the fluid downcast pipes and, being cooled by the coolant in the jacket, also descends. The fluid media thus reaching the lower part of the tank flow radially inward and again become an upwardly rising current.

In this manner, the fluid media within the tank, while undergoing the above described convectional flow, are cooled by the inner wall surface of the cooling jacket and by the inner wall surfaces of the fluid downcast pipes installed within the cooling jacket. As a result, the temperature of the fluid media within the tank can be maintained at a specific value. This temperature of the fluid media can be controlled by controllably adjusting the flow rate or the temperature of the coolant being supplied through the cooling jacket.

The nature, utility, and further features of this invention will be more clearly apparent from the following detailed description with respect to preferred embodiments of the invention when read in conjunction with the accompanying drawings, which are briefly described below.

DETAILED DESCRIPTION OF THE INVENTION

As conducive to a full understanding of this invention, the general nature and accompanying problems of conventional cooling systems of cultivation tanks will first be briefly described.

Figure 11A:
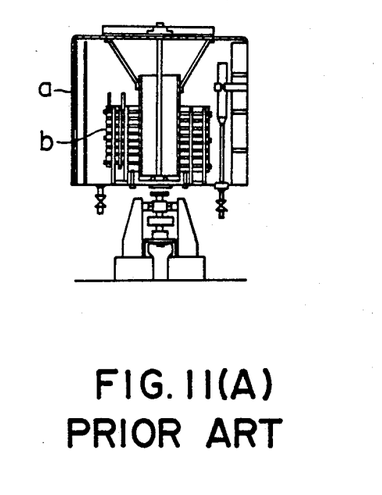
FIGS. 11(A), 11(B), 11(C), and 12 are schematic elevational views, some in vertical section, respectively showing examples of cultivation tanks with cooling systems of the prior art.
Figure 11B:
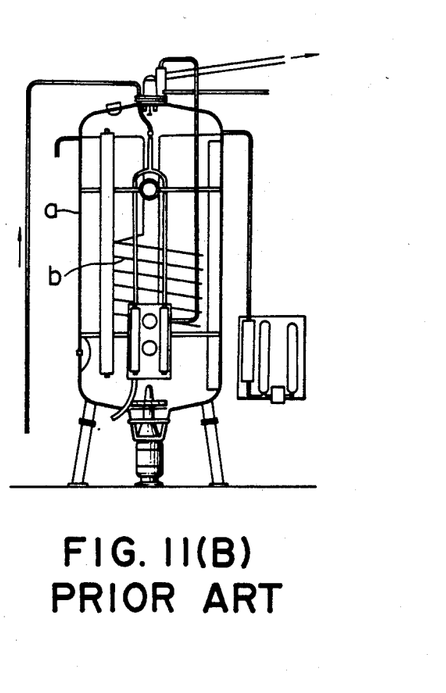
Figure 11C:
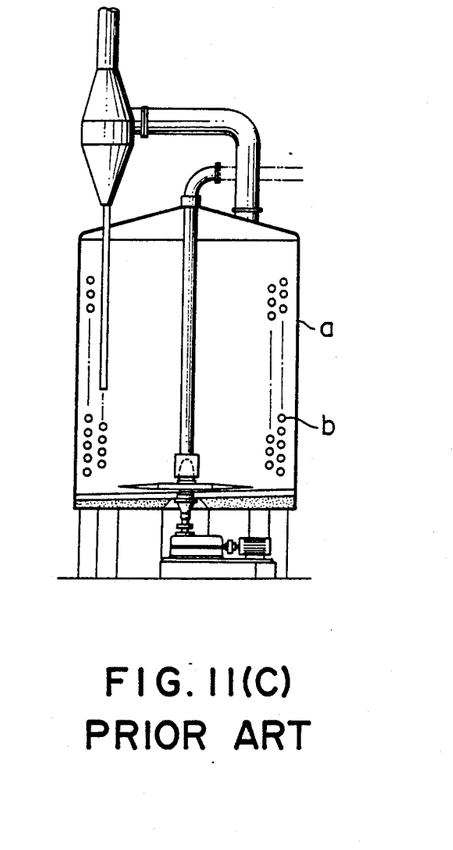
Figure 12:
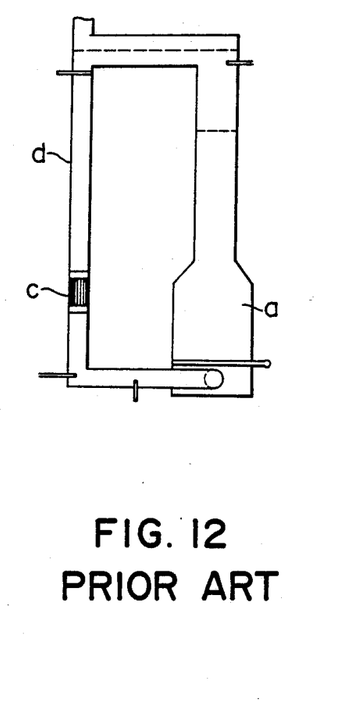

The aforementioned Waldhof, Frings, and Vögelbusch types of cooling systems of cultivation tanks known heretofore are respectively shown FIGS. 11(A), 11(B), and 11(C). In each of these tanks a, a coil-shaped cooling pipe b is installed. By passing a coolant through the cooling pipe b, the fluid media in the tank a are cooled. Another known cooling system as illustrated schematically in FIG. 12 has an external cooler c outside of the tank a. This cooler c is installed in an external part of a cooling liquid circuit d, one part of the coolant flows through a cultivation tank a. As mentioned hereinbefore, these known tanks have been accompanied by problems such as poor washability of their interiors and complicated construction.

These problems of the prior art have been overcome by this invention, one example of which will now be described with reference to FIGS. 1 through 4. This example of the aerobic-cultivation tank of the invention has a tank structure 1 of vertical cylindrical shape which comprises a cylindrical middle barrel 1a, an upper part 1b of the shape of a short cylinder with dome-shaped top, and a lower part 1c of dish or basin shape. The middle barrel 1a is fixed around its upper end coaxially to an annular upper tube plate 14 and around its lower end coaxially to an annular lower tube plate 15. A cylindrical inner wall 13 is fixed around its lower end to the circular inner rim of the lower tube plate 15. Around its part which is at a certain distance below its extreme upper end, this inner wall 13 is fixed to the circular inner rim of the upper tube plate 14.

Figure 1:
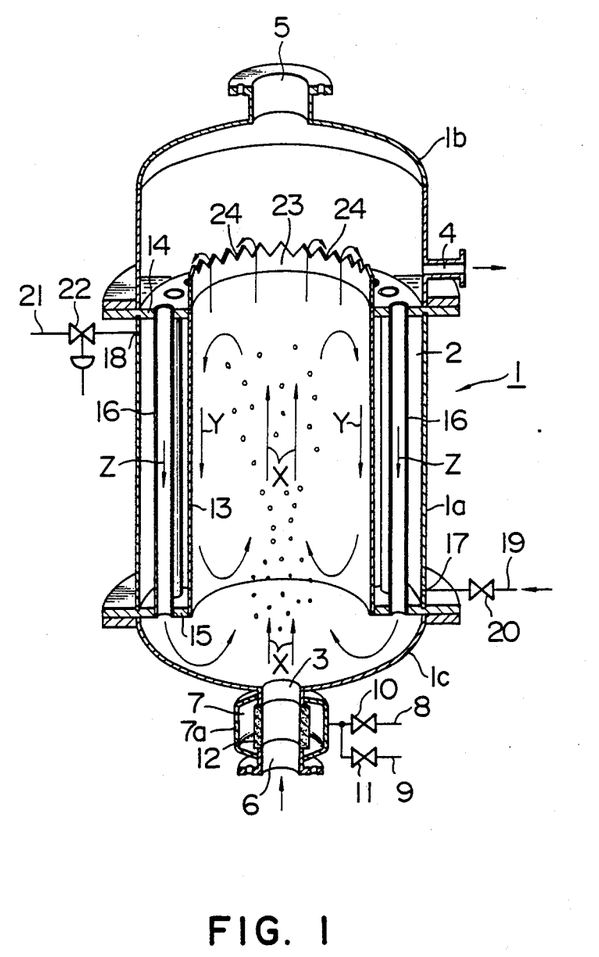
FIG. 1 is a perspective view, in vertical section, showing one example of the aerobic-cultivation tank according to the invention.
Figures 2, 3, 4:
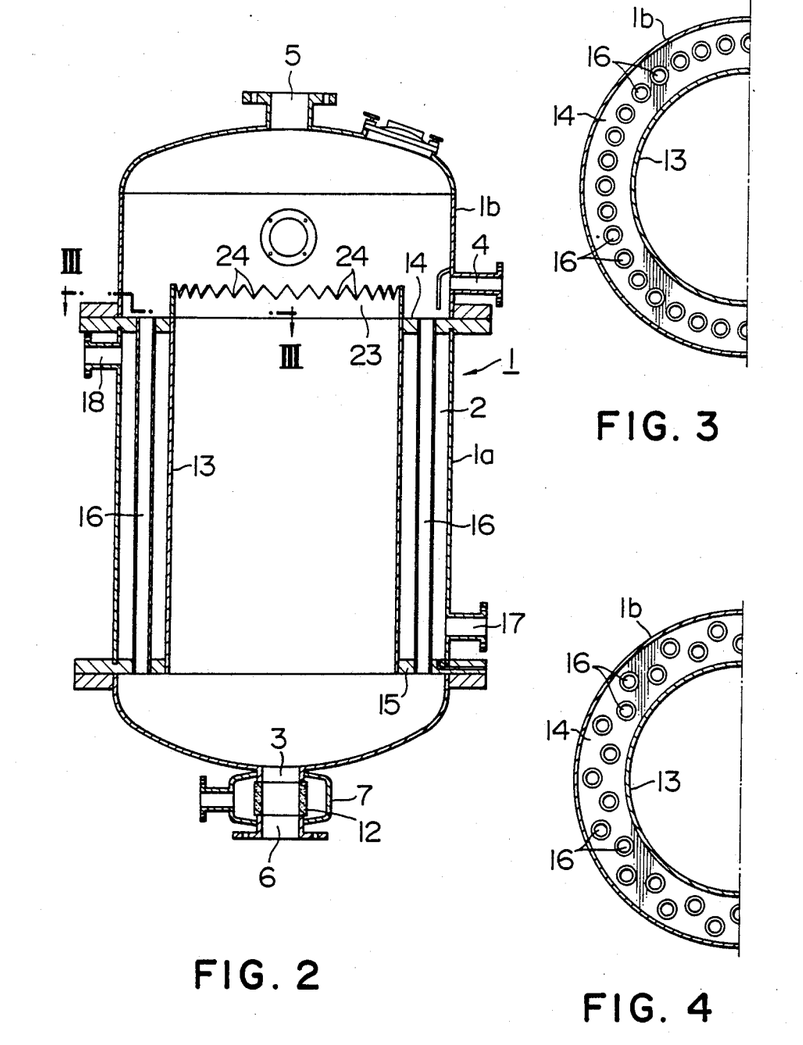
FIG. 2 is an elevation, in vertical section, of the same tank.
FIG. 3 is a half section taken along the stepped surface indicated by line III—III in FIG. 2.
FIG. 4 is a half section, similar to FIG. 3, showing a modified example.

The cylindrical wall of the middle barrel 1a, the inner wall 13, and the inner parts of the upper and lower tube plates 14 and 15 thus form a closed cylindrical space which functions as a cooling jacket 2.

The lower part 1c of the tank structure 1 is provided at its bottom center part with a fluid media supply port 3. The upper part 1b of the tank structure 1 is provided at its top center part with a gas extraction port 5 and at a side part thereof with a fluid media discharge port 4. A fluid media supply pipe 6 is connected to the fluid media supply port 3 by way of a cylindrical porous filter 12 interposed therebetween. This filter 12 is enclosed within a cylindrical housing 7a forming an annular chamber 7 therearound. An air supply system 8 for aeration and a steam supply system 9 for supplying washing steam are connected respectively by way of valves 10 and 11 to the housing 7a to communicate with the chamber 7. Thus, through the porous filter 12, air and steam can be supplied into the lower part 1c and other interior parts of the tank structure 1 except for the cooling jacket 2.

Within the cooling jacket 2 are provided several fluid downcast pipes 16, 16, ... extending vertically between the upper and lower tube plates 14 and 15 and arranged parallelly in a circle at regular intervals around the cooling jacket 2. The upper end of each pipe 16 is passed through and fixed in a leakproof manner to the upper tube plate 14 and is open to the interior of the upper part 1b of the tank structure 1. Similarly the lower end of each tube 16 is passed through and fixed to the lower tube plate 15 and is open to the interior of the lower tank part 1c.

A coolant is supplied through a coolant supply pipe 19 and a valve 20 into a coolant inlet 17 of the cooling jacket 2 at a lower part thereof. After circulating through the jacket 2 while absorbing heat, this coolant is discharged from the jacket through a coolant outlet 18, a valve 22, and a coolant discharge pipe 21.

The upper part of the inner wall 13 of the cooling jacket 2 projects upward above the upper tube plate 14, thereby forming a ring-shaped weir 23. The upper edge of this weir 23 has therearound a consecutive circle of cutouts 24, 24, ..., whereby the weir 23 has a serrated upper edge. The shape of each of the cutouts 24, 24, ... is not limited to a triangle but may be any suitable figure such as a rectangle or a semicircle.

The fluid downcast pipes 16, 16, ..., as viewed in plan view as in FIG. 3, may be disposed on a single common circle with a center coinciding with the centerline of the tank 1. Alternatively, the pipes 16 may be arranged in some other regular polar pattern such as the zig-zag pattern shown in FIG. 4.

The aerobic-cultivation tank of the above described construction according to this invention is operated in the following manner.

The coolant is supplied into the cooling jacket 2 through the coolant inlet 17; fluid media are supplied through the fluid supply pipe 6 and the fluid media supply port 3 into the lower tank part 1c; and air is supplied from the air supply system 8, the porous filter 12, and the port 3 in the lower tank part 1c. The air thus supplied thereupon assumes the form of bubbles in the fluid media and rises, thereby inducing an upward flow of the fluid media in the central part of the tank as indicated by the arrows X. The portion of the fluid media in contact with the inner wall surface of the inner wall 13 of the cooling jacket 2 is cooled and flows downward as indicated by the arrows Y. Thus, a natural convectional circulation occurs in the middle part of the tank.

As the level of the fluid media rises in this middle part of the tank, the upper portion of the fluid media overflows through the cutouts 24, 24, ... of the weir 23 at the upper part of the inner wall 13 and, as it is agitated, flows down onto the upper surface of the upper tube plate 14. This portion of the fluid media then flows downward through the fluid downcast pipes 16, 16, ..., being cooled by the coolant circulating through the cooling jacket 2 and thereby becoming a descending fluid flow as indicated by the arrows Z. This descending fluid thus flows into the lower tank part 1c to join the rising fluid at the central part of the tank. As a net result, a convection circulation of the fluid media arises naturally in the arrow directions X, Y, and Z within the cultivation tank. The temperature of the fluid media within the tank therefore tends to become uniform, and at the same time a gentle agitating action is obtained.

In one instance of the above described example of the aerobic-cultivation tank of this invention, in the case of fluid media capacity of 8.5 m$^3$, the area $\delta_1$ of the inner wall surface of the inner wall 13 becomes equal to $nD_1h = 14.07$ m$^2$, and the heat transfer area $\delta_2$ of the fluid downcast pipes 16 becomes equal to $Nnd_1h = 25.32$ m$^3$. Here, $D_1$ is the inner diameter of the cylindrical inner wall 13 of the cooling jacket 2; h is the height of the inner wall 13; d1 is the diameter of the fluid downcast pipes 16; and N is the number of pipes 16. Thus, the heat transfer area becomes approximately three times that of the conventional cultivation tank, and, in addition, the improvement in convection circulation results in an even more effective cooling.

Figure 5:
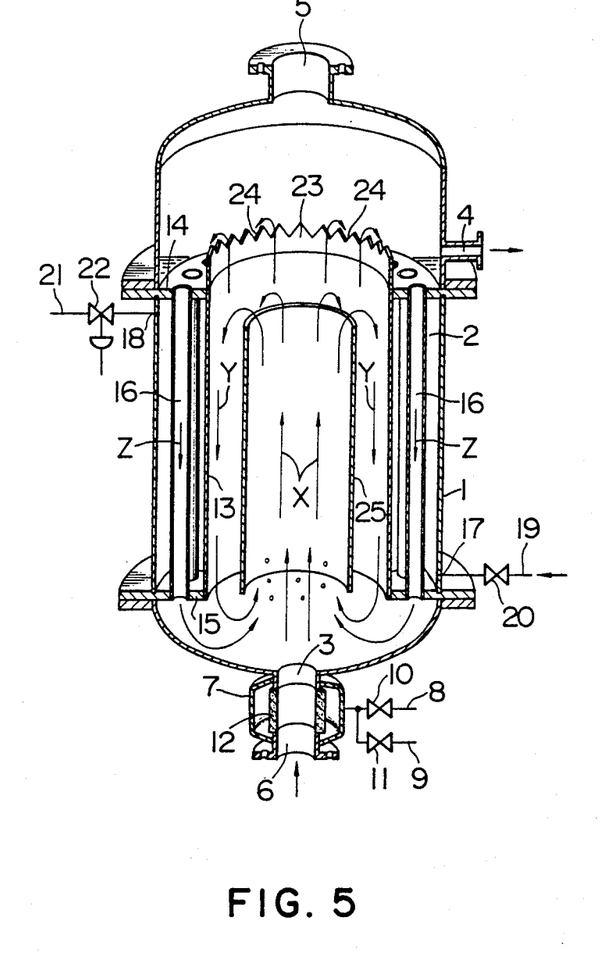
FIGS. 5 and 6 are perspective views, in vertical section, respectively showing other examples of the aerobic-cultivation tank of the invention.

In another example of the invention as shown in FIG. 5, a hollow cylinder 25 is disposed concentrically inside of the inner wall 13 to function as a distinct partition between rising flow and descending flow of the flow inside of the inner wall in order to produce an even more smooth convection circulation of the fluid media. This hollow cylinder 25 has substantially the same height as the cooling jacket and a diameter which is approximately ½ of that of the inner wall 13. The other features of construction and operation of this example are similar to those of the preceding example. Those parts of this example which are the same as or equivalent to corresponding parts in FIGS. 1 through 4 are designated by like reference numerals. Detailed description of such parts will not be repeated. The same applies to further embodiments of the invention described hereinafter.

In the operation of this tank, the rising current flows principally through the interior of the hollow cylinder 25 as indicated by the arrows X and is rectified by the inner wall surface of this cylinder 25 and thus caused to flow smoothly. Furthermore, the descending current flows principally through the space between the inner wall 13 of the cooling jacket 2 and the hollow cylinder 25 as indicated by the arrows Y. Thus, the natural convection circulation of the fluid within the tank is carried out smoothly, and an effective cooling with agitation is attained.

Figure 6:
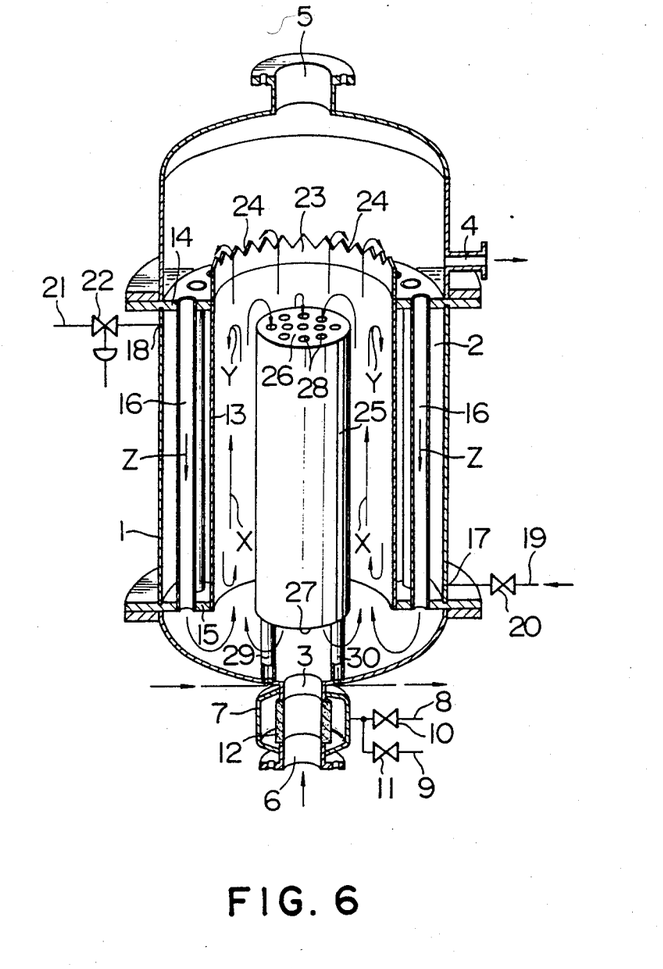

In still another example of the aerobic-cultivation tank as shown in FIG. 6, the hollow cylinder 25 of the preceding example is converted into a structure of a cooler or heat exchanger. The upper and lower ends of the hollow cylinder 25 are closed by upper and lower plates 26 and 27. Fluid downcast pipes 28, 28, ... are disposed vertically in spaced-apart arrangement within the hollow cylinder 25, the upper and lower ends of these pipes 28, 28, ... being passed through and fixed in a leakproof manner to the upper and lower plates 26 and 27 and being open to the upper and lower parts of the interior of the tank. A coolant is caused to circulate through the interior of the cylinder 25 and in contact with the exterior surface of the pipes 28, 28, ..., being supplied and discharged through a coolant supply pipe 29 and a coolant discharge pipe 30.

In the functioning of the cooler structure described above, the descending flow of the fluid media passes through the interiors of the fluid downcast pipes 28, 28, within the hollow cylinder 25, and the fluid media are thus cooled by the coolant circulating within the cylinder 25. Therefore this construction is effective in increasing the cooling effect when it is applied to cultivation tanks of large size. Other features of construction and operation of this example are similar to those of the preceding example.

Cleaning and maintenance of sanitation of each of the above described tanks can be achieved by the following procedures.

(1) The fluid media are drained out of the tank, and then water is supplied through the fluid supply pipe 6 into the tank up to the overflow level, or steam containing 0.5 to 2.0% of NaOH admixed therein is supplied into the tank.

(2) The coolant in the cooling jacket 2 is drained out through the coolant inlet 17, and then, through this inlet, steam is introduced to cause boiling and flushing action.

(3) In the case where the contamination is slight, the above procedures (1) and (2) are not carried out, and steam is introduced directly into the tank 1 to carry out autoclaving.

The construction of the tank can be modified in a number of ways to suit the cultivation. In the case where a small heat transfer area is sufficient, the number of fluid downcast pipes 16, 16, ... can be reduced. In such a case, a measure other than that of selecting the number of fluid downcast pipes 16 is to close a specific number of already installed pipes with a plug stopper to select the number of effective pipes. Furthermore, instead of constructing the inner wall structure of the cooling jacket 2 completely around the tank in the circumferential direction, it may be installed at intermittent intervals.

In still another example of the aerobic-cultivation tank as shown in FIGS. 7 through 10, the vertical tank structure 31 is long in its height relative to its diameter and is provided with a cooling jacket 32 formed between the barrel part of the tank structure 31, a hollow cylindrical inner wall 40, an upper tube plate 41, and a lower tube plate 42. Within this cooling jacket 32 are installed several fluid downcast pipes 44 similarly as in the preceding examples. These pipes 44 are arranged in a regular pattern on three concentric circles as viewed in plan view in FIG. 8. The tank structure 31 is closed at its lower end by a bottom end plate 39 of dish shape, which is provided at its center with a single fluid media supply port 34. Around this fluid media supply port 34 are provided a plurality of air supply pipes 33, fluid agent injection ports 38 and a manhole 45 as well. This aerobic-cultivation tank is suitable for use in the case where a great quantity of oxygen is required. By these features of this tank, the natural circulation of the fluid therewithin is promoted. Moreover, agitation and cooling effects due to natural convection flow are obtained efficiently, and the aeration efficiency is greatly improved.

Figure 7:
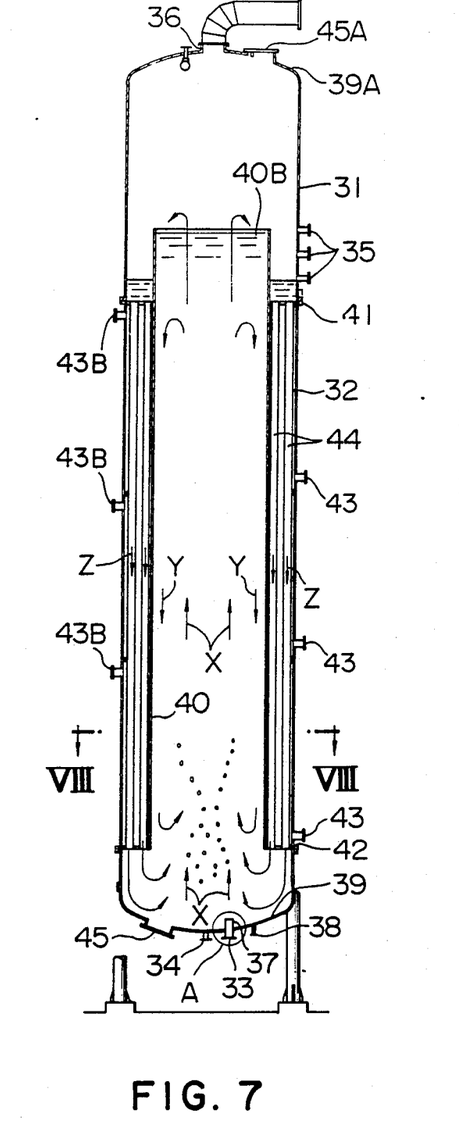
FIG. 7 is a perspective view, in vertical section, showing still another example of the aerobic-cultivation tank of the invention.
Figure 8:
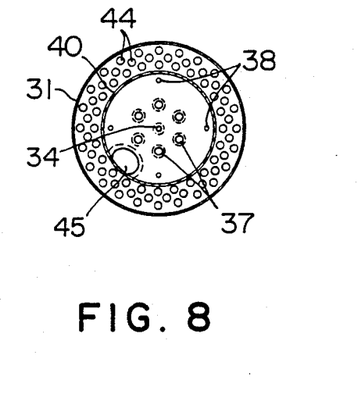
FIG. 8 is a section taken along the cross-sectional plane indicated by line VIII—VIII in FIG. 7.
Figure 9:
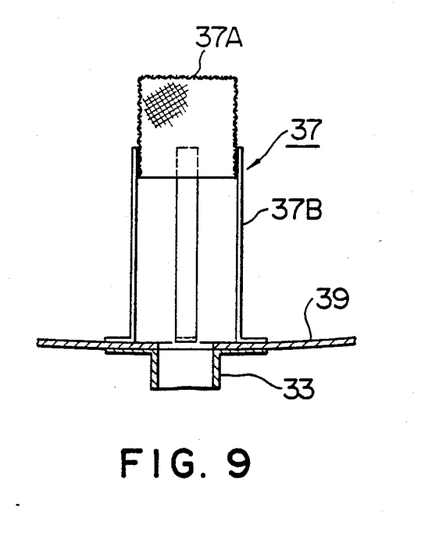
FIG. 9 is a fragmentary, relatively enlarged view of the bottom part A in FIG. 7.
Figure 10:
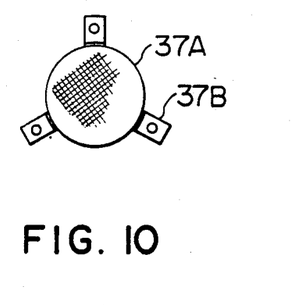
FIG. 10 is a top view orthogonal to FIG. 9.

In this tank, the upper part of the cylindrical inner wall 40 projects through and above the upper tube plate 41, forming a cylindrical weir 40B. The tank structure 31, at its middle barrel part forming the outer wall of the cooling jacket 32, is provided at different height levels with a number of coolant inlets 43 and coolant outlets 43B. The top end plate 39A is provided with a manhole 45A and a centrally disposed gas discharge port 36. The bottom end plate 39 is provided with a manhole 45. A plurality of fluid media outlets 35 are provided through the upper part of the tank structure 31 above the upper tube plate 41.

Particularly in the instant example, air nozzles 37 are connected respectively to the plurality of air supply pipes 33 connected through the bottom end plate 39 around the central port 34 for supplying fluid media and function to supply air into the interior of the tank. As shown in detail in FIGS. 9 and 10, each of these air nozzles 37 comprises a stainless-steel strainer 37A of a screen size of the order of 4-mesh and a plurality of mounting legs 37B which are fixed at their lower ends to the bottom end plate 39, and on which the strainer 37A is supported.

The aerobic-cultivation tank of the above described construction is operated in the following manner. Fluid media are supplied through the fluid media supply port 34 into the bottom part of the tank structure 31, and, as a fluid agent such as $H_2SO_4$, $NH_4OH$, or $Na_2SO_3$ is injected through the fluid agent injection ports 38 into the bottom part of the tank structure 31, air is supplied thereinto through the air supply pipes 33. As this air thus supplied through the air supply pipes 33 is thereupon rectified by the strainers 37A of the air nozzles 37 connected to the air supply pipes 33, it is blown into the fluid media. This air thereby assumes the form of bubbles and ascends to induce a rising current through the interior of the cylindrical inner wall 40, as indicated by arrows X in FIG. 7, as it performs aeration of the fluid media.

Furthermore, the fluid media contacting the inner walls surface of the inner wall 40 of the cooling jacket 32 is thereby cooled and becomes a descending current as indicated by arrows Y, whereby a natural convection circulation is established within the tank. Some of the fluid media overflows over the upper rim of the weir 40B at the upper extremity of the inner wall 40, and, as it is agitated, flows down onto the upper tube plate 41 at the top of the cooling jacket 32 and then flows downward through the fluid downcast pipes 44 as indicated by arrows Z. This fluid is thereby cooled by the cooling jacket and, becoming a descending flow, reaches the bottom part of the tank. Then this fluid, becoming mixed with ascending fluid, again rises, thus circulating through the interior of the tank.

As a consequence of these flows of the fluid, a natural convectional flow of the fluid media as indicated by the arrows X, Y, and Z is established within the tank. The temperature of the fluid media is thus rendered uniform, and at the same time good agitation and aeration are obtained. Particularly in the instant example, air is blown at a flow velocity of 30 cm/sec. into the tank through the strainers 37A, whereby ample agitation and aeration of the fluid media become possible without the use of a perforated filter.

While the foregoing disclosure relates to aerobic-cultivation tanks in which agitation and aeration due to natural convectional circulation are the principal effects of operation, the teachings of this invention are applicable, of course, also to cultivation tanks provided with agitators and further to aerobic-cultivation tanks of designs other than those described above.

Because of the constructional and operational features of the aerobic-cultivation tank according to this invention as described above, whereby natural circulation of the fluid media is obtained, agitation and cooling effects due to natural convectional flow are achieved with high efficiency and undesirable rises in the temperature of the fluid media are prevented. Thus the cultivation efficiency is remarkably increased. Furthermore, since the cooling jacket is provided in a concentric state at the inner peripheral part of the tank structure, its heat transfer area is large, whereby the cooling effectiveness is greatly increased. Moreover, since cooling pipes of coil shape are not present within the tank structure, the washability of the tank is good, and various other beneficial features such as simplified construction are afforded.

What is claimed is:

1. An aerobic-cultivation tank of vertical type comprising:
   a closed outer tank structure of cylindrical shape;
   a cylindrical inner wall secured concentrically to the inner wall surface of the said tank structure;
   an internal cooling jacket defined concentrically between the inner wall surface of said tank structure and the outer wall surface of said cylindrical inner wall and having a cylindrical space therebetween for accommodating a coolant;
   a plurality of fluid downcast pipes passed vertically through said space and being open at upper and lower ends thereof to upper and lower interior parts of the tank structure;
   means for passing the coolant through said space; and
   means for supplying fluid media into the tank structure;
   whereby when the fluid media are supplied into the tank structure to a level above the upper ends of the fluid downcast pipes, the fluid media overflow into and descend through said pipes, while being cooled, into a lower interior part of the tank, while a portion of said fluid media in contact with the inner surface of the cooling jacket is also cooled and descends, the fluid media body as a whole thereby undergoing a natural circulatory flow due to convection.

2. An aerobic-cultivation tank as claimed in claim 1 in which said cylindrical inner wall projects upward to form a cylindrical weir.

3. An aerobic-cultivation tank as claimed in claim 2 in which the upper rim of said cylindrical weir is provided with cutouts and thereby has a serrated profile.

4. An aerobic-cultivation tank as claimed in claim 1 in which a hollow cylindrical structure with open ends is disposed within and coaxially with said tank structure at a middle part thereof.

5. An aerobic-cultivation tank as claimed in claim 1 in which said tank structure has a dish-shaped lower part provided at its center with a fluid media supply port, to which is connected a fluid media supply pipe via a cylindrical porous filter interposed therebetween and enclosed within a cylindrical housing forming therearound an annular chamber to which are connected an air supply system for supplying air for aeration and a steam supply system for supplying washing steam, both said air and said steam, upon being supplied first into said chamber, through said porous filter, and then through said fluid media supply port.

6. An aerobic-cultivation tank as claimed in claim 1 in which said tank structure has a dish-shaped lower part provided at its center with a fluid media supply port and at the same time provided with a plurality of air supply pipes disposed in a regular arrangement around a circle concentric with said center.

7. An aerobic-cultivation tank as claimed in claim 6 in which said air supply pipes comprise a wire mesh strainer.

8. An aerobic-cultivation tank as claimed in claim 5 in which said fluid downcast pipes are disposed, as viewed in plan view, in a regular zig-zag pattern on at least two circles of different diameter which are concentric about the axial center of the cooling jacket.

9. An aerobic-cultivation tank of vertical type comprising:
   a closed outer tank structure of cylindrical shape;
   a cylindrical, open ended inner wall secured concentrically to the inner wall surface of said tank structure, the ends of said inner wall terminating short of the ends of said tank structure;
   an internal cooling jacket defined concentrically between the inner wall surface of said tank structure and the outer wall surface of said cylindrical inner wall and having a cylindrical closed space therebetween for accommodating a coolant;

a plurality of fluid downcast pipes passed vertically through said space and being open at upper and lower ends above and below, respectively, said space and opening into upper and lower interior parts of the tank structure;

means for passing the coolant through said space; and means for supplying fluid media into the tank structure and into said cylindrical inner wall; whereby when the fluid media are supplied into said inner wall to a level above the upper end thereof, the fluid media overflow said inner wall and descend through said pipes, while being cooled, into a lower interior part of the tank, while a portion of said fluid media in contact with the inner surface of the cooling jacket is also cooled and descends, the fluid media body as a whole thereby undergoing a natural circulatory flow due to convection.

* * * * *